United States Patent [19]

Sabatino

[11] Patent Number: 5,299,564
[45] Date of Patent: Apr. 5, 1994

[54] EXPANDABLE DILATOR AND METHOD FOR INTRAOCULAR SURGERY

[75] Inventor: Robert C. Sabatino, Newtown Square, Pa.

[73] Assignee: Kabi Pharmacia Ophthalmics Inc., Monrovia, Calif.

[21] Appl. No.: 949,702

[22] Filed: Sep. 23, 1992

[51] Int. Cl.⁵ .............................................. A61B 17/02
[52] U.S. Cl. ..................................... 128/20; 606/198; 128/3
[58] Field of Search ................. 128/20; 606/107, 162, 606/166, 198, 204.25; 623/4, 5, 6; 604/289, 294; 152/511

[56] References Cited

U.S. PATENT DOCUMENTS

| | | | |
|---|---|---|---|
| 2,012,211 | 8/1935 | Willig | 152/511 |
| 2,526,164 | 10/1950 | Slemmons | 152/511 |
| 4,387,706 | 6/1983 | Glass | 128/20 |
| 4,782,820 | 11/1988 | Woods | 128/20 |
| 5,109,875 | 5/1992 | Gottlieb | 128/898 |

Primary Examiner—C. Fred Rosenbaum
Assistant Examiner—Noelle Kent Gring
Attorney, Agent, or Firm—Poms, Smith, Lande & Rose

[57] ABSTRACT

In accordance with the disclosed device and method a highly-corrugated hollow miniature torus is introduced into the pupillary opening in the eye of a person. Then, the torus is expanded by introduction of fluid therein, so that it engages and dilates the marginal edge of the iris. An intraocular surgical procedure is then performed, following which the torus is contracted and removed. A valve is employed to control the introduction and discharge of the fluid.

6 Claims, 3 Drawing Sheets

EXPANDABLE DILATOR AND METHOD FOR INTRAOCULAR SURGERY

BACKGROUND OF THE INVENTION

In conventional dilation techniques used in intraocular surgery, the pupil is dilated by a mydriatic agent. However, when mydriatic agents are employed the surgeon does not know, with certainty, either the diameter or duration of the dilation. When the pupil is—or becomes—insufficiently dilated the performance of the surgeon is hindered. Not only may the patient results then be adversely affected, but the instruments used by the surgeon may injure intraocular structures, for example causing iritis.

Conventional dilation techniques have the further drawback of requiring the use of miotic agents to constrict the pupil after the surgical procedure is completed.

In some instances, the above-indicated techniques may require alternative performance of an iridectomy.

Because of the problems caused by the conventional mydriatic-agent-followed-by-miotic-agent steps, attempts have been made to provide dilation means that are mechanical instead of pharmacological. The mechanical dilation means known to applicant are, however, characterized by various shortcomings. The shortcomings include one or more of the following: 1) inability to effect precise control of the amount of dilation, 2) relative difficulty or complexity of insertion, removal, and use, and 3) failure to shield the surrounding edge of the iris, etc., from surgical instruments.

SUMMARY OF THE INVENTION

The present expandable dilator and method advance intraocular surgical capabilities and, consequently, enhance patient results.

A device sized to fit in the pupillary space or opening of a person is inserted through a small incision in the cornea, and is then maneuvered into such space so as to be adjacent the inner edge of the iris. The device is adapted to be expanded to any size not injurious to the iris, and in accordance with one aspect of the present invention is so expanded by fluid.

Stated more definitely, the device comprises a generally hollow torus that is adapted, in response to introduction of fluid, to expand and to increase the diameter of the pupillary space to a desired diameter, preferably one that enhances the surgeon's visual ability to perform various intraocular surgical techniques such as capsulorhexis, cataract removal by Phaco or ECCE, etc. The device and method are such that the space is maintained at the desired size throughout the surgery. Upon substantial completion of the procedure, the fluid is withdrawn from the device, causing it to contract to a size such that it may be readily removed through the incision.

The preferred hollow expandable device is a toroidal bellows associated with ribs that are shaped in complementary manner relative to the marginal edge of the iris, so that the device will maintain effective contact with such marginal edge during the expansion and thereafter.

DETAILED DESCRIPTION OF THE PREFERRED EMBODIMENT

Figure 1:
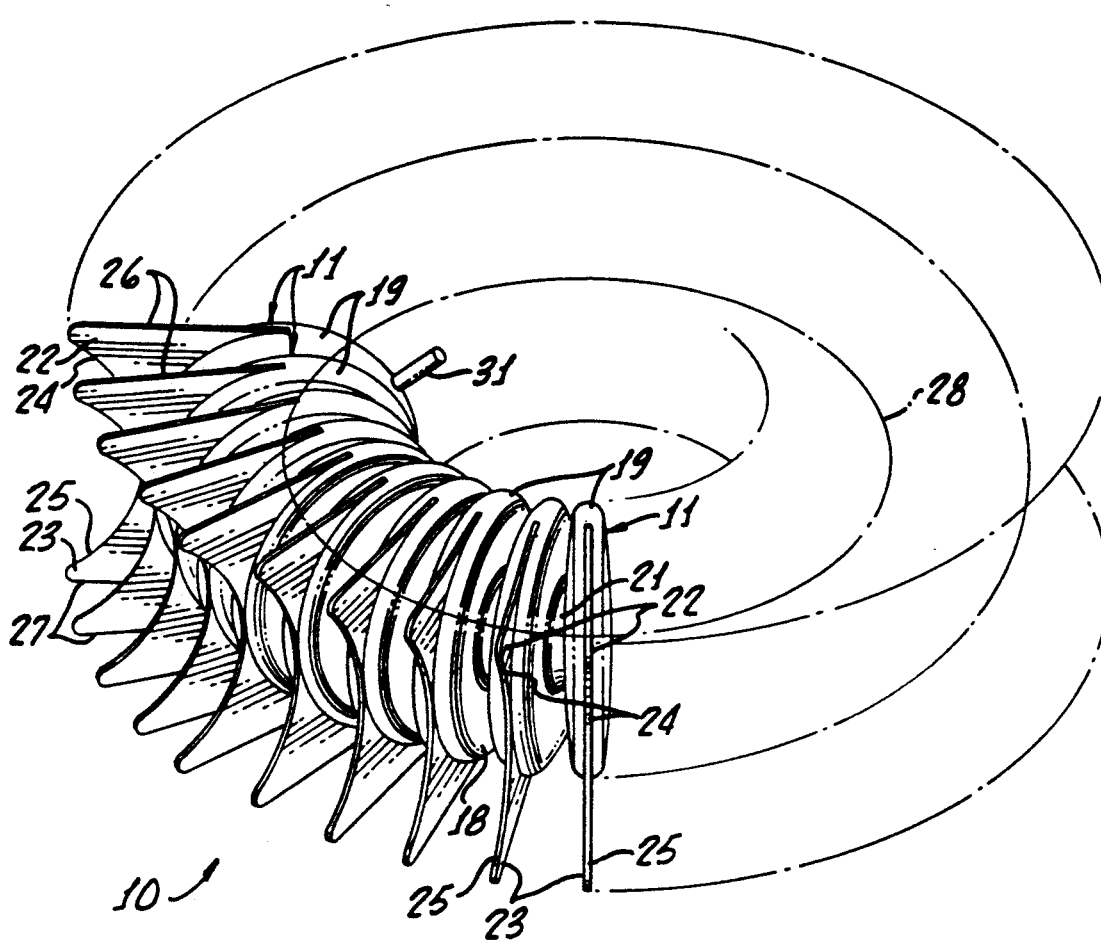
FIG. 1 is a greatly enlarged view of the preferred embodiment of the present device.
Figure 2:
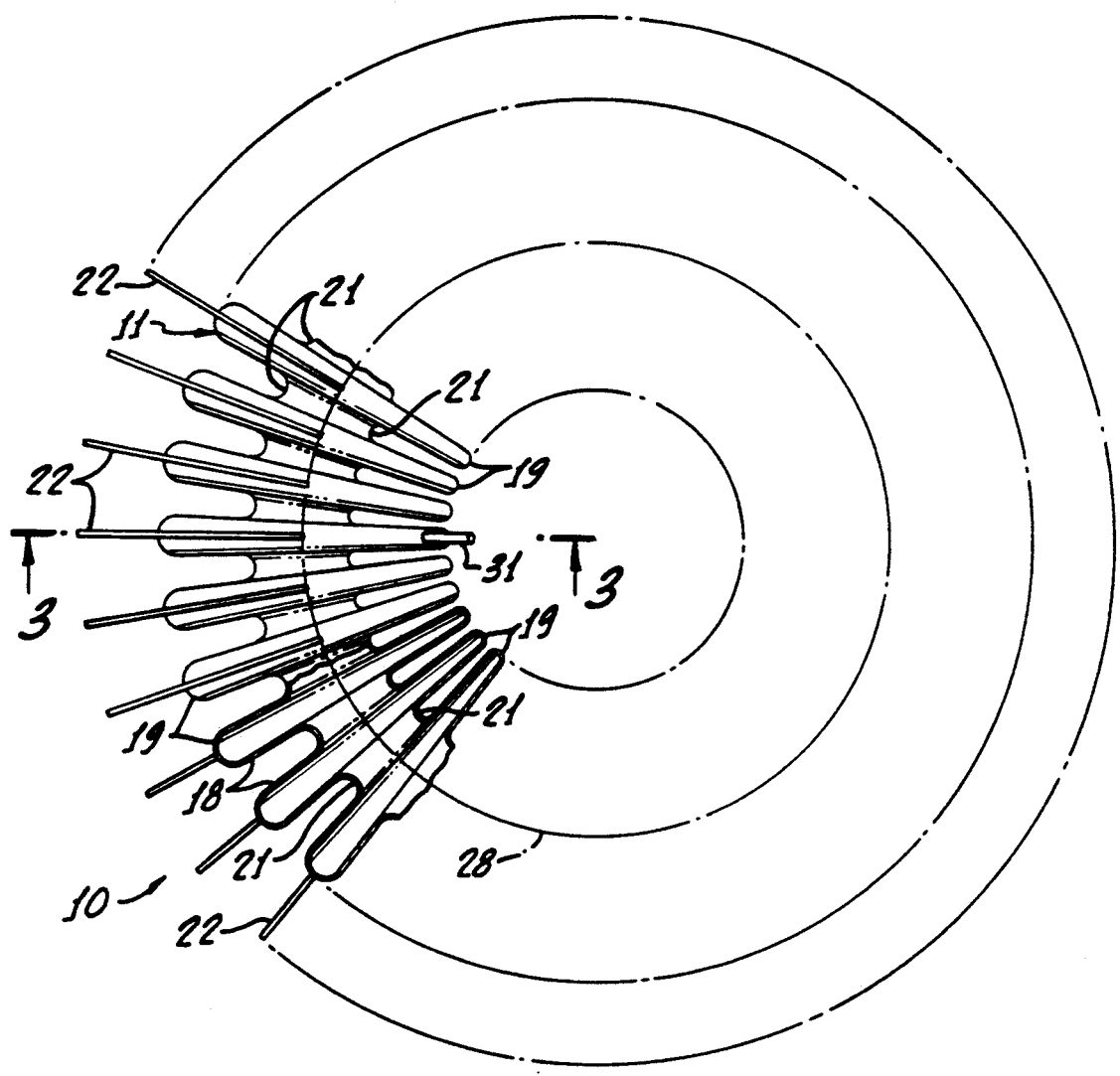

Referring to FIG. 1, a preferred form of the dilator is shown at 10, and comprises a hollow torus 11 that is shaped as a bellows. Thus, the torus has a corrugated or undulating flexible wall throughout the entire circumference of the torus. When in its natural uninflated, or free, condition as shown in FIG. 2, the dilator 10 has such a diameter as to fit loosely in the pupillary space of a person, parallel to and adjacent the lens 14.

Figure 5:
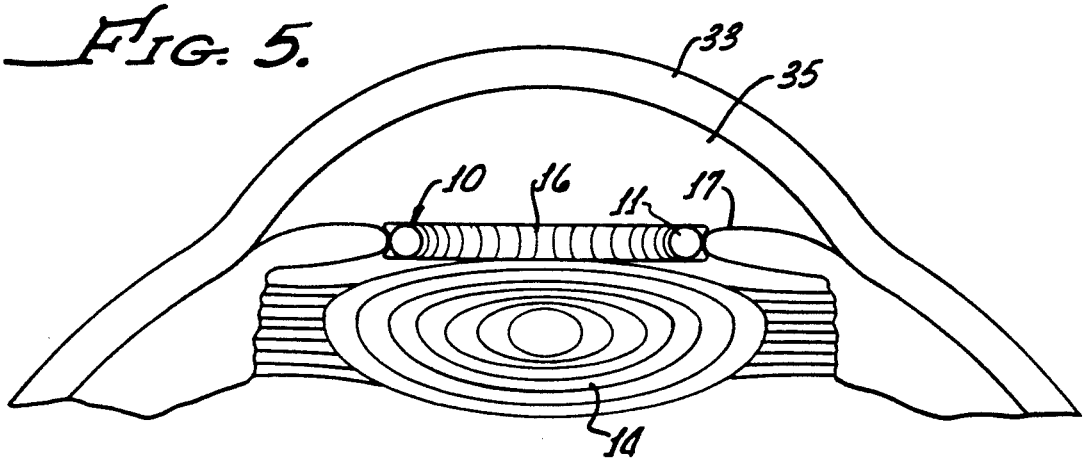

The number of corrugations or undulations of the bellows wall, and the radial dimensions of the undulations, and the wall thickness and flexibility, are such that torus 11 may be fluid-enlarged to a greatly expanded condition such as the one illustrated in FIG. 5. The size of the expanded torus, and the radial dimension of each region of the torus, are such that there is formed in the pupillary space an access opening 16 through which instruments may be inserted during the intraocular surgery. The size of access opening 16 is sufficiently large to facilitate introduction of the surgical instruments, but not so large as to injure the iris 17.

Figure 3:
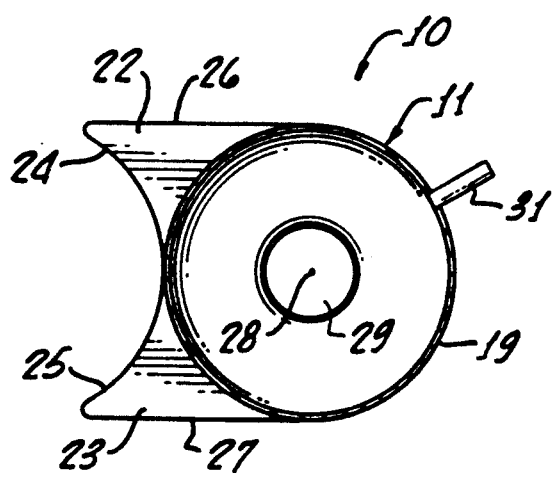
FIGS. 2 and 3 are, respectively, horizontal and radial sections of the device shown in FIG. 1, FIG. 3 being taken at line 3—3 of FIG. 2.

Referring again to FIG. 2, the torus 11 comprises a multiplicity of corrugations or undulations 18 each of which has a ridge 19 and a groove 21. Each ridge 19 lies in a radial plane containing the axis of torus 11, and each groove 21 lies in a radial plane containing such axis. The ridges, and the grooves, are equally spaced about the full circumference of the torus. As shown at the left in FIG. 2, each ridge is preferably rounded or arcuate in section, as is each groove 21. Each ridge, and each groove, is circular in shape in the above-specified planes, as shown in FIG. 3. The radiuses of the inner portions of each ridge 19 are (as shown in FIG. 2) much smaller than are the radiuses of the outer portions of each ridge. The same applies relative to each groove 21, but in lesser degree.

Means are provided about the peripheral portion of torus 11 to engage and seat against the marginal edge of iris 17. This keeps the dilator 10 in correct position during and after said expansion. In the preferred embodiment, there is one such means provided on each ridge 19 about the exterior of the torus. As best shown in FIGS. 2 and 3, such means comprise upper and lower ribs 22 and 23, respectively, that for each corrugation 18 lie in a plane containing the axis of torus 11 and also containing the center of each ridge 19. The ribs have, respectively, generally concave outer edges 24,25 which cooperate to form a single curved line that is generally complementary to the shape of the iris edge.

In addition, the ribs 22,23 have, respectively, upper and lower straight horizontal edges 26,27 that are respectively tangential to ridges 19 at the extreme top and bottom ridge portions. Stated otherwise, the edges 26,27 intersect, at ridges 19, a hypothetical cylinder having an axis coincident with the axis of the torus and having its cylindrical wall containing the circular center line 28 (FIGS. 2 and 3) of the toroidal central space defined by the inner regions of the undulations 18 adjacent grooves 21.

The torus 11 is preferably molded of a suitable synthetic resin, and is preferably molded integrally with the described ribs 22,23. Alternatively, the ribs may be bonded to the torus subsequent to molding of the latter.

The wall of torus 11 defines a chamber 29 that is continuous in the preferred embodiment. Chamber 29 comprises not only the spaces within the undulations 18 but also the toroidal central space indicated above.

Figure 4:
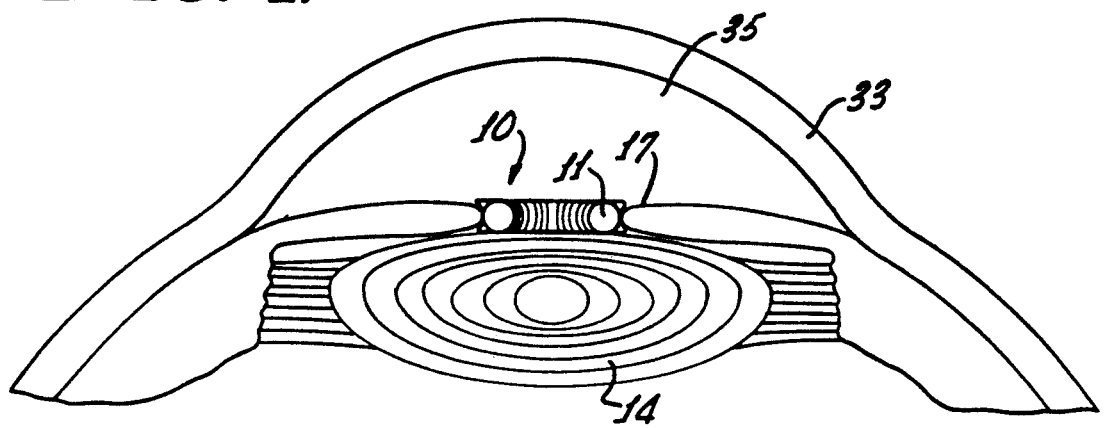
FIGS. 4 and 5 are schematic views respectively illustrating the device in substantially retracted and expanded conditions in the pupillary space, the incision being not shown.

In accordance with a major aspect of the present invention, fluid is injected into chamber 29 in order to inflate the torus 11 and cause it to expand first from the free condition of FIG. 2 to the partially-expanded condition of FIG. 4, and then from the partially-expanded condition of FIG. 4 to the fully (or substantially fully)-expanded state of FIG. 5. Furthermore, after the intraocular surgery is substantially completed, fluid is withdrawn from the chamber 29 so as to effect contraction of the torus 11 to such a diameter that it may be removed.

A valve is provided in order to permit introduction and withdrawal of the fluid, and to prevent outflow of the fluid during continuance of the surgical procedure. The valve is indicated schematically at 31 in FIGS. 2 and 3. It comprises a short tubular element including a check valve, and which is mounted on one of the ridges 19 at an interior region thereof.

The tubular passage (not shown) in valve 31 communicates with chamber 29 in torus 11, and is associated with a check valve (not shown) to permit fluid to be introduced into chamber 29 while preventing outflow of fluid from that chamber until such time as outflow is desired. The construction is such that introduction of a hypodermic needle into the tubular passage in valve 31 opens the check valve and permits outflow of the fluid through such needle.

Alternatively, a continuous small-diameter flexible tube of substantial length is connected to torus 11 in communicating relationship with chamber 29, such tube extending to the exterior of the eye. The tube has a shutoff valve and a control valve associated therewith, and communicates with a source of pressure and suction. In such alternative construction, fluid is passed through the tube from the pressure source to chamber 29 to inflate the torus. Then, after the procedure is substantially completed, suction is applied to the tube in order to draw fluid from chamber 29 in a rapid manner for rapid deflation of the torus and consequent reduction in the diameter thereof.

In the preferred form, the torus has sufficient resilience that it will return to its free condition shown in FIG. 2 in response to opening of valve 31, the resilience of the torus forcing the fluid through the valve. The viscosity of the fluid employed for inflation of the torus is caused to be sufficiently low to permit this result, and to expedite inflation/deflation of the torus.

Description of the Method, and Further Description of Advantages

Figure 6:
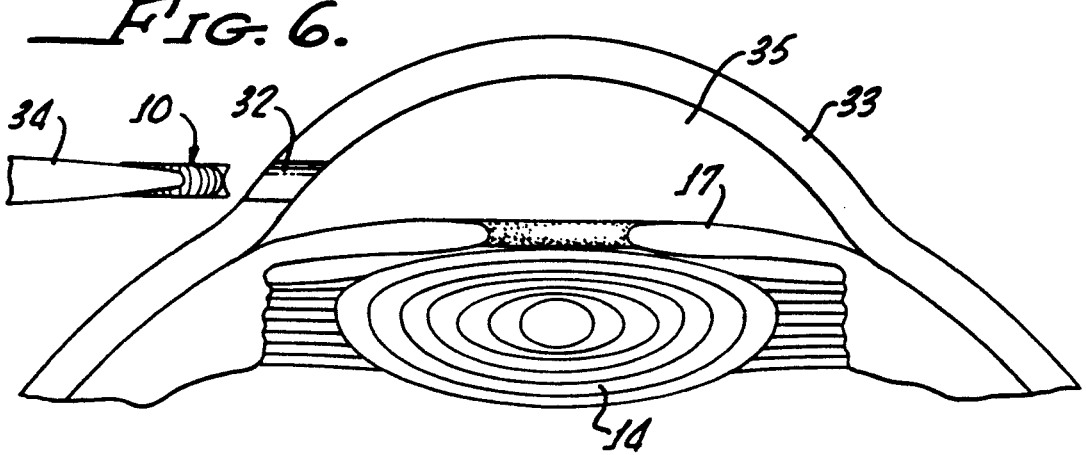
FIG. 6 is a schematic view indicating the incision and illustrating the contracted device as being held by forceps just prior to being inserted through the incision and maneuvered into the desired position.

Referring especially to FIG. 6, a small incision 32 is made in cornea 33 adjacent the corneal-scleral junction. A suitable instrument 34 is employed to introduce the dilator 10—when in the small-diameter condition of FIG. 2—through incision 32 into the anterior chamber 35, following which the dilator 10 is maneuvered into the pupillary opening, namely to the position shown in FIG. 4 but with the dilator 10 in a somewhat smaller-diameter condition than is illustrated in FIG. 4.

Then, the surgeon introduces fluid into chamber 29 (FIGS. 2 and 3) within the torus 11 and thereby expands the circumference and diameter of the dilator so as to achieve a relatively large-diameter access opening 16 within the torus, as shown in FIG. 5. The diameter of access opening 16 is regulated by the surgeon by regulating the amount of fluid introduced into the chamber 29.

The surgical procedure or technique is then performed using an instrument or instruments that are passed through the access opening 16. It is pointed out that the dilator 10 acts as a mechanical barrier between such instruments and the edge of iris 17, etc., thus reducing the possibility of inadvertent contact between an instrument and the iris.

In accordance with one method of introducing fluid and thus inflating the dilator 10, the forceps-like element indicated fragmentarily and schematically at 34 in FIG. 6 is employed to grasp the dilator and also somewhat pinch it to a smaller-diameter condition than that illustrated in FIG. 2. One form of forceps fits in the recesses—adapted to receive the iris edge—defined by edges 24,25 of ribs 22,23 (FIG. 3). Then, after the dilator has been inserted through the incision 32 it is released, following which the surgeon grasps the valve 31 (FIGS. 2 and 3) with forceps and then inserts the tip of a hypodermic needle, which is mounted on a hypodermic syringe, longitudinally into the valve 31. When the dilator 10 is in the proper position in the pupillary opening, as described above, the surgeon injects fluid from the hypodermic syringe and through the needle and the valve 31 into chamber 29 within the torus, thereby expanding the torus to the diameter of (for example) FIG. 5, all as determined by the amount of fluid injected. The needle is then withdrawn, and the valve 31 prevents outflow of the fluid.

After the capsulorhexis, cataract removal, etc., has been completed, the surgeon again inserts a hypodermic needle into the valve 31 and withdraws the fluid from chamber 29 within the torus. The natural resilience of the synthetic resin forming the torus returns the torus to its small diameter condition illustrated in FIG. 2, following which the surgeon removes the dilator from the pupillary opening and from the anterior chamber 35 through incision 32 (FIG. 6), and then closes the incision.

In accordance with an alternative manner of introduction, the surgeon employs a special hypodermic needle having a flange thereon, the location of the flange being such that there may only be a limited amount of insertion of the needle tip into the valve 31. With such construction, the tip may be inserted into valve 31 prior to introduction of the dilator through the incision. In such instance, the needle itself serves as a tool that supports the dilator as it is being introduced through the incision and then moved into position in the pupillary opening. The needle is employed to inflate the dilator, is then removed and the surgical procedure is performed as indicated above.

In accordance with a third alternative, the above-indicated long tube is employed as stated above and is connected to the dilator so as to communicate at all times with chamber 29 therein. Fluid is then passed back and forth between the exterior of the eye and the chamber 29 for both inflation and contraction purposes.

During the surgical procedure, there is no fluid flow unless the ophthalmologist wishes to change the degree of dilation.

The present dilator may be delivered to the ophthalmologist in a sterile container, the dilator being coated with viscoelastic material such as (for example) that sold under the trademark "Healon" by Pharmacia company of New Jersey.

It is emphasized that there is no need for use of mydriatic agents or miotic agents to dilate and contract the pupil. Furthermore, there is no uncertainty as to the diameter or duration of the dilation. The access opening 16 remains at the diameter set by the surgeon throughout the entire continuance of the intraocular surgery. Accordingly, there is no danger that a small pupil will occur and thereby hinder the surgeon's performance or affect patient results. In addition, there is no danger that inadequate dilation may result in injury and thus cause undesirable conditions such as iritis.

Stated in another manner, the present apparatus and method guarantee the dilation as to both uniformity and diameter throughout the entire procedure. This is done without an iridectomy and without any pharmacological agents. There is single intraocular placement and expansion at the start of surgery, and there is stability until removal of the dilator just prior to close.

The present apparatus and method increase the surgeon's visual ability to better perform the surgical techniques that are required. The dilator protects the entire circular iris membrane sphincter, and also protects the adjoining ciliary body structures, against contact by surgical instruments.

It is pointed out that the edges 24,25 of the ribs 22,23 may have contours somewhat different than what is shown in FIG. 3. It is also pointed out that the fluid employed may be either liquid or gas.

It is emphasized that pressurization of the dilator causes it to elongate circumferentially, and therefore engage the circular iris sphincter and enlarge the pupillary space to a desired access-opening diameter such as is shown in FIG. 5.

The foregoing detailed description is to be clearly understood as given by way of illustration and example only, the spirit and scope of this invention being limited solely by the appended claims.

What is claimed is:

1. A device for dilating the pupillary space defined by the marginal edge of an iris in an eye during intraocular surgery, said device comprising:
   a hollow torus formed of fluid-impervious flexible resilient material and dimensioned to fit in said pupillary space, said torus having a corrugated or undulating wall constructed so that the diameter of said torus will increase in response to injection of fluid into said torus;
   injection means through which fluid may be injected into said torus, effecting said increase in diameter of said torus and consequent dilation of said pupillary space; and
   iris-engaging means including rib means provided on the outer side of said torus and shaped generally to receive said marginal edge of said iris, said rib means mating with said marginal edge and effecting said dilation of said pupillary space in response to injection of fluid into said hollow torus.

2. The device of claim 1, in which said corrugated or undulating wall of said torus has a multiplicity of corrugations or undulations that are substantially equally spaced about the circumference of said torus.

3. The device of claim 2, in which said rib means are respectively provided on crest portions of said corrugations or undulations.

4. The device of claim 3, in which said rib means have lower sides disposed in planes substantially parallel to the central medial plane of said torus and meeting said torus at the extreme lower regions thereof.

5. The device of claim 2, in which said injection means comprises a valve communicating with the interior of said torus.

6. A method of dilating the pupil of the eye of a person preparatory to and during an intraocular surgical procedure, said method comprising:
   (a) providing a fluid-expansible element so sized that, prior to expansion, it will fit in the pupillary space in the eye of a person,
   (b) making an incision in the cornea of the eye of a person,
   (c) inserting said expansible element through said incision and maneuvering said expansible element into the pupillary space in said eye,
   (d) introducing fluid into said expansible element to expand the same and cause it to engage the marginal edge of the iris in said eye and thereby effect dilation of said pupillary space,
   (e) maintaining said expansible element thus fluid-expanded during continuance of a surgical procedure relative to said eye, and
   (f) discharging said fluid from said expansible element upon completion of the surgical procedure an effecting contraction of said expansible element, and
   (g) withdrawing said contracted expansible element from said eye.

* * * * *